United States Patent [19]

Dolgin et al.

[11] Patent Number: 5,108,379
[45] Date of Patent: Apr. 28, 1992

[54] FLUID PASSING APPARATUS WITH MEANS FOR COVERING THE SAME

[75] Inventors: Stuart M. Dolgin, 95 Belvedere Dr., Syosset, N.Y. 11791; Philip Torbet, Brookville, N.Y.

[73] Assignee: Stuart Dolgin, Syosset, N.Y.

[21] Appl. No.: 709,490

[22] Filed: Jun. 3, 1991

Related U.S. Application Data

[60] Division of Ser. No. 446,213, Dec. 5, 1989, Pat. No. 5,047,016, which is a division of Ser. No. 241,352, Sep. 7, 1988, Pat. No. 4,898,589, which is a continuation-in-part of Ser. No. 166,046, Mar. 9, 1988, abandoned, which is a continuation-in-part of Ser. No. 135,581, Dec. 21, 1987, abandoned.

[51] Int. Cl.$^5$ ............................................. A61M 5/32
[52] U.S. Cl. ..................................... 604/198; 604/263
[58] Field of Search ............... 604/192, 187, 198, 263, 604/110

[56] References Cited

U.S. PATENT DOCUMENTS

| | | | |
|---|---|---|---|
| 3,134,380 | 5/1964 | Armao | 604/198 |
| 4,416,663 | 11/1983 | Hall | 604/198 |
| 4,564,054 | 1/1986 | Gustavsson | 604/198 |
| 4,725,267 | 2/1988 | Vaillancourt | 604/198 |
| 4,775,369 | 10/1988 | Schwartz | 604/263 |
| 4,795,432 | 1/1989 | Karczmer | 604/110 |
| 4,804,371 | 2/1989 | Vaillancourt | 604/198 |
| 4,898,589 | 2/1990 | Dolgin et al. | 604/198 |
| 4,915,697 | 4/1990 | DuPont | 604/192 |
| 4,917,672 | 4/1990 | Terndrup et al. | 604/263 |

Primary Examiner—Stephen C. Pellegrino
Assistant Examiner—Ralph A. Lewis
Attorney, Agent, or Firm—Watov & Kipnes

[57] ABSTRACT

Apparatus for passing a fluid into or out of a warm-blooded animal which includes a fluid containing body, a needle assembly releasably mountable on the exterior surface of the body, a plunger for urging a fluid into or out of the body and an externally mounted cap or retraction device for automatically covering the needle after it has been used and preventing the needle from reentering the aperture in the body.

8 Claims, 13 Drawing Sheets

FLUID PASSING APPARATUS WITH MEANS FOR COVERING THE SAME

This is a divisional application of Ser. No. 07/446,213 filed Dec. 5, 1989, now U.S. Pat. No. 5,047,016 which is a divisional of application Ser. No. 07/241,352 filed Sep. 7, 1988, now U.S. Pat. No. 4,898,589, issued Feb. 6, 1990, which is a continuation-in-part application of U.S. Ser. No. 07/166,046 filed on Mar. 9, 1988, now abandoned, which is a continuation-in-part application of U.S. Ser. No. 07/135,581 filed on Dec. 21, 1987, now abandoned.

FIELD OF THE INVENTION

The present invention is directed to an apparatus for passing a fluid through an aperture including means for conveniently and effectively covering the apparatus after use and particularly to syringes in which the needle is automatically covered after use by a cap or is retracted into the barrel of the syringe and is thereafter prevented from reentering the aperture.

BACKGROUND OF THE INVENTION

Over the past several years, the medical profession has been extremely concerned about exposure of medical personnel to patients and fluid samples infected with communicable diseases, and particularly AIDS. In an effort to minimize the risk of infection, medical personnel have donned masks, gloves and other protective devices in the treatment of patients.

One of the ways in which medical personnel can be subjected to a communicable disease is through the handling of devices which are designed to inject or withdraw a fluid from a patient (e.g., a hypodermic syringe, and the like). Once the syringe is contacted with the patients blood through the injection process, it becomes a high-risk potential carrier of infectious disease.

Accordingly, the medical profession has recognized the need for a convenient and efficient means of protecting medical personnel from contaminated needles. One of the first major advancements in this area was the development of the disposable syringe.

The most common disposable syringe contains a fluid-containing barrel and a movable plunger therein. The top end of the barrel has a collar having an open ended cavity with grooves for removably securing therein a needle assembly. The needle assembly includes a rigidly fixed needle mounted in a base which is screwed into the cavity of the collar. The needle is covered with an elongated snap-on cap which is removed prior to use. In order to operate the syringe, a suitable needle assembly with the cap in place is twisted onto the collar of the syringe. The cap is removed and the needle is ready to be injected into the patient. After use, the cap is held in one hand and the needle assembly in the other hand. The user must then carefully place the cap over the needle and push downward until the cap snaps in place. The entire syringe may then be discarded. Such syringe devices enable a barrel to be used interchangeably with any size needle since the barrels and needle assemblies are typically packaged separately.

Despite the reduction in handling time, such disposable syringes have not allayed the concerns of the medical profession regarding the risk of infection by an exposed contaminated needle. This is because the elongated cap must be slowly and very carefully secured over the exposed needle thereby requiring complete concentration by the user.

In the often hectic and sometimes frantic performance of medical services, the user of such hypodermic needles often misaligns the cap and needle leading to needle pricks of the hand or arms. Such accidents occur because it is difficult to cover the needle properly under typical medical facility conditions. Accordingly, there have been efforts to provide a convenient and efficient means of covering contaminated needles to prevent post-use needle pricks.

Such efforts have focused on two methods of covering the needle. The first is to employ a cover which can be moved upwardly and over the needle and the second is to retract the needle within the barrel of the syringe. The use of a cover is exemplified by Sampson et al., U.S. Pat. No. 4,425,120; Mitchell, U.S. Pat. No. 4,631,057; Strauss, U.S. Pat. No. 4,664,645; and Fox, U.S. Pat. No. 4,695,274.

Syringe devices of the second type employing means for retracting the needle into the body of the syringe are shown in Vining et al., U.S. Pat. No. 4,507,117, Jagger et al., U.S. Pat. No. 4,592,744, DeLuccia, U.S. Pat. No. 4,675,005 and Haber et al U.S. Pat. No. 4,710,170.

The aforementioned devices have not gained commercial acceptance because they are complicated, difficult to manufacture and/or require substantial redesigning of the previously described standard syringe. More specifically, some such devices have a prepacked needle of a particular size which is loaded from within the barrel. As a result, the needle assemblies are not interchangeable with the standard barrel which adds to the cost of the syringe and makes the syringe less efficient to use. Furthermore, some of the prior devices do not permit external loading of the needle assembly on the top exterior surface of the barrel which also adds to the cost of the syringe.

Commercial efforts at capping contaminated needles have essentially rejected the complex and costly devices disclosed by the aforementioned patents. Instead, hospitals, clinics and individual medical practitioners have opted for systems which remove and store contaminated needles using devices which are separate and apart from the syringe itself.

One such device is sold under the trademark VACUSAFE and includes a container for storing contaminated needles. The top of the container has a V-shaped hole with a serrated or gripping side that grips the needle assembly placed therein and dislodges it from the syringe when the syringe is rotated by the user.

Another such device is sold under the trademark DESTRUCTOCLIP which is similar to VACUSAFE but has the added feature of cutting off the tip of the needle while the syringe is held in the hole in the top of the container.

While these systems are effective once the syringe is inserted through the opening of the device, they are disadvantageous because the contaminated needle must be moved in its exposed condition from the patient to the place where the storage container is located. Thus, the contaminated needle is exposed for an unacceptable period of time during which the risk of accidental contact with the user, the patient or other personnel is high.

It is therefore an object of the invention to provide a convenient and effective manner of promptly covering contaminated parts of a fluid passing device.

It is a further object of the invention to provide a disposable syringe in which a contaminated needle is promptly removed from any possible detrimental contact with the user, the patient or other personnel.

It is a still further object of the invention to provide a means of covering the needle of a disposable syringe of the type in which the needles and barrels are interchangeable.

It is another object of the invention to provide a disposable syringe in which the needle assembly is covered by a cap activated from a location which is remote from the contaminated needle tip.

It is another object of the invention to provide a disposable syringe in which the contaminated needle assembly is retracted into the barrel of the syringe from a location which is remote from the contaminated needle tip.

It is a still further object of the invention to provide a disposable syringe in which the used needed is prevented from reentering the aperture of the needle assembly.

SUMMARY OF THE INVENTION

The present invention is generally directed to an apparatus for passing a fluid through an aperture in which it is desirable to cover the apparatus and protect the user from contamination after the apparatus has been used. In one form of the invention, the fluid passing apparatus is designed to inject or withdraw a fluid from a warm-blooded animal or the tissue of a warm-blooded animal.

The apparatus comprises a body adapted to contain the fluid such as a barrel of a syringe or the body may itself contain a removable vial for the receiving of a fluid (e.g., blood) from a warm-blooded animal.

The size of the body or the vial contained within the body is unlimited and therefore the invention is not limited by the amount of fluid which is passed through the apparatus. Typical examples of such devices include the standard barrel type syringe, blood drawing apparatus and the like.

The apparatus of the invention also includes a fluid passing means such as a needle assembly in flow communication with the barrel which is adapted to penetrate the animal tissue. The needle assembly is affixed to the top exterior surface of the barrel either by rotation into a groove or press-fitting so that different sized needles may be used interchangeably with a standard barrel. The invention also includes means for covering the fluid passing means either by a cover which is activated at a location remote from the fluid passing means or by retracting the fluid passing means within the barrel of the device. Means are also provided for automatically preventing the needle from reentering the aperture upon activation of the cover or by retraction of the needle into the barrel.

BRIEF DESCRIPTION OF THE DRAWINGS

The following drawings in which like reference characters indicate like parts are illustrative of embodiments of the invention and are not meant to limit the scope of the invention as encompassed by the claims forming part of the application.

DETAILED DESCRIPTION OF THE INVENTION

Referring to the drawings and particularly to FIGS. 1, 4, 7 and 11, the fluid passing device 2 generally includes a barrel section 4 having a top end 6 having mounted thereon a collar 8. The barrel section 4 is typically cylindrical, but may be four-sided having a substantially square-configuration as described hereinafter, and has a wall 10 defining a cavity 12 for receiving or ejecting a fluid such as blood or a drug solution. The barrel section 4 may also contain a standard vial (not shown) for storing blood received from the patient.

Within the cavity 12 is a plunger 14 including a head section 16 having a wall 18 which communicates with the interior of the wall 10 of the barrel 4 to provide a sealed chamber 20 which contains the fluid. The volume of the sealed chamber 20 increases when the plunger 14 is pulled back and decreases when the plunger 14 is pushed forward due to the seal formed by the contact of the wall 18 of the head section 16 with the interior surface of the wall 10. The plunger 14 has a stem 22 connected to the head section 16 at one end and to a handle (not shown) at the other end as is well known in the art.

The fluid passing device 2 also includes a needle assembly 24 which includes a base 26 and a neck region 28. A needle 30 or other fluid passing means is rigidly fixed within the neck region 28. As shown in the drawings, the needle 30 is relatively short for the sake of convenience. It should be understood that the present invention is adapted to facilitate the use of any size length and diameter needle.

Figure 1:
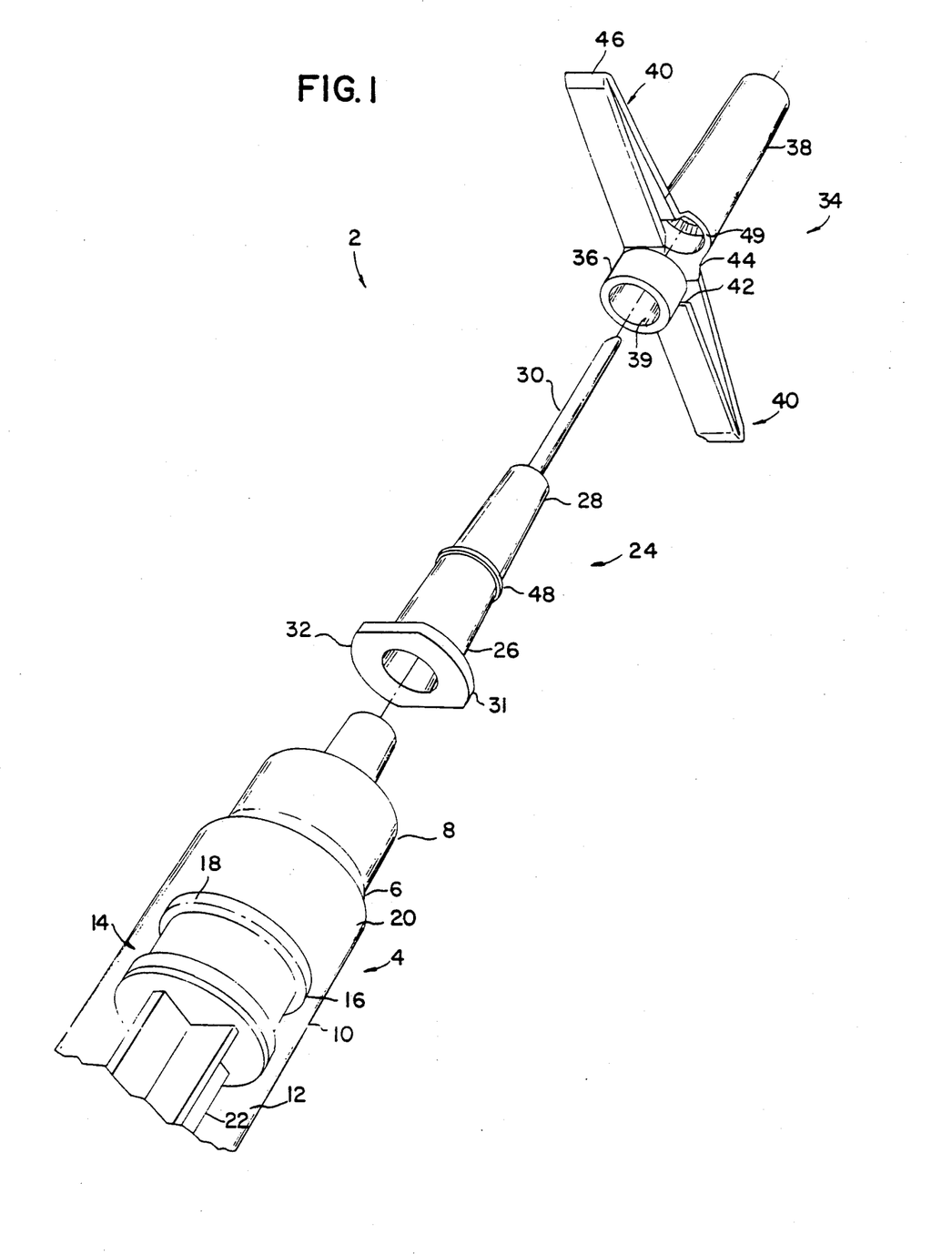
FIG. 1 is a partial exploded view of one embodiment of a syringe in accordance with the present invention employing a double-winged cap for covering the needle.
Figure 2:
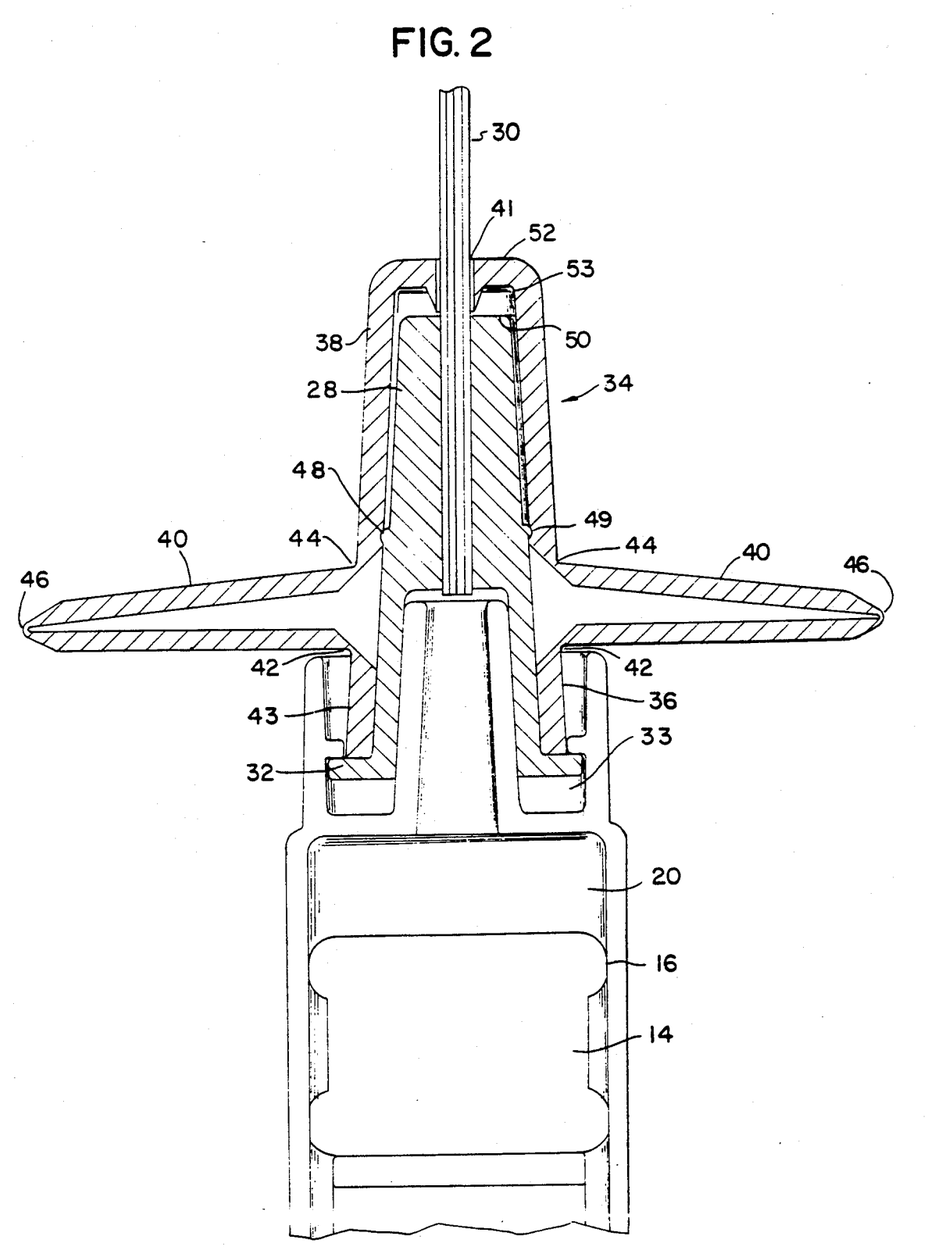
FIG. 2 is a partial cross-sectional view of the embodiment shown in FIG. 1.

The needle assembly 24 also includes a securing means 32 for attaching the needle assembly 24 to the collar 8 of the fluid passing device 2. As shown in FIGS. 1 and 2, the securing means 32 may include an arcuate side surface 31 which serves as a thread that may be reversibly locked within a groove 33 (see FIGURE 2) within the collar 8 by rotating the needle assembly 24.

The present invention also includes means 34 for covering the needle 30 after it has been used, the cover means 34 being movable from a retracted position in which the needle 30 is exposed ready for use to an extended position where the cover means 34 extends above and over the needle 30.

Referring to FIGS. 1 and 2, the cover means 34 comprises a bottom portion 36 and a top portion 38, an axial hole 39 therethrough and an aperture 41 through which the needle 30 protrudes when the cover means 34 is in the retracted position. A pair of folded arm sections 40 are connected to the bottom 36 and top 38 portions through hinges 42 and 44, respectively. The arms 40 are extendable about a flexible hinge section 46 and hinges 42 and 44. The cover means 34 including the arms 40, hinges 42, 44 and 46 are preferably made of a flexible plastic such as polypropylene or polyethylene.

Between the base 26 and the neck region 28 of the needle assembly 24 is a flange 48. In factory assembly, the cover means 34 is inserted over and secured to the needle assembly 24 by placing the needle 30 within the axial hole 39 and moving the cover means 34 downward and over the flange 48 until the interior surface 43 of the bottom portion 36 is taper locked or otherwise securely locked onto the base 26. The top portion 38 is retracted until the annular groove 49 is releasably locked over the flange 48.

The fluid passing device 2 shown in FIG. 1 may be sold as individual components or as a self-contained unit. When sold as individual components, the needle 30 of the needle assembly 24 is capped with a standard snap-on type elongated cap. In the form of a self-contained unit, the cover means 34 is secured to the needle assembly 24 by the interlocking of the flange 48 within the groove 49. The standard elongated cap is secured over at least the portion of the needle 30 which protrudes beyond the top of the axial hole 39 when the arms 40 of the cover 34 are in the retracted position shown in FIGS. 1 and 2. The present invention, however, is not limited to any particular manner of packaging the components of the invention.

As best seen in FIG. 2, the needle 30 is exposed and ready for use when the elongated cap (not shown) is removed and the arms 40 are in the radially extended position corresponding to the cover 34 being in the retracted position as previously described. After use, the contaminated needle 30 is covered by pushing the arms 40 inwardly at the hinge section 46. This causes the flange 48 to disengage from the annular grove 49 and the top portion 38 of the cover 34 to move upwardly along the axis of the needle 30 until the top end 52 of the cover 34 extends above and over the needle 30.

The cover 34 of the present invention is also provided with means for insuring that the needle 30 can not reenter the aperture 41 once the cover 34 is extended above and over the needle 30. This is accomplished, for example, by making one of the arms 40 (e.g. the right arm) slightly longer than the other arm. This causes the cover 34 to move radially in the direction of the shorter arm once the top end 52 of the cover 34 has been raised above the needle 30. In this way, the tip of the needle 30 will come to rest on the right hand interior surface 50 (see FIG. 2) of the top end 52 of the cover 34 corresponding to the longer arm 40. Of course, the needle 30 will come to rest on the opposite bottom surface of the top end 52 if the left arm 40 is made slightly longer than the right arm 40.

Re-emergence of the needle 30 through the aperture 41 may also be prevented by forming the aperture 41 with a downwardly extending conical tapered side 53. When the cover 34 is raised above the end of the needle 30 and the needle 30 comes to rest on the bottom interior surface 50, the needle 30 is prevented from moving radially toward the aperture 41 by the downwardly extending tapered side 53.

Figure 3:
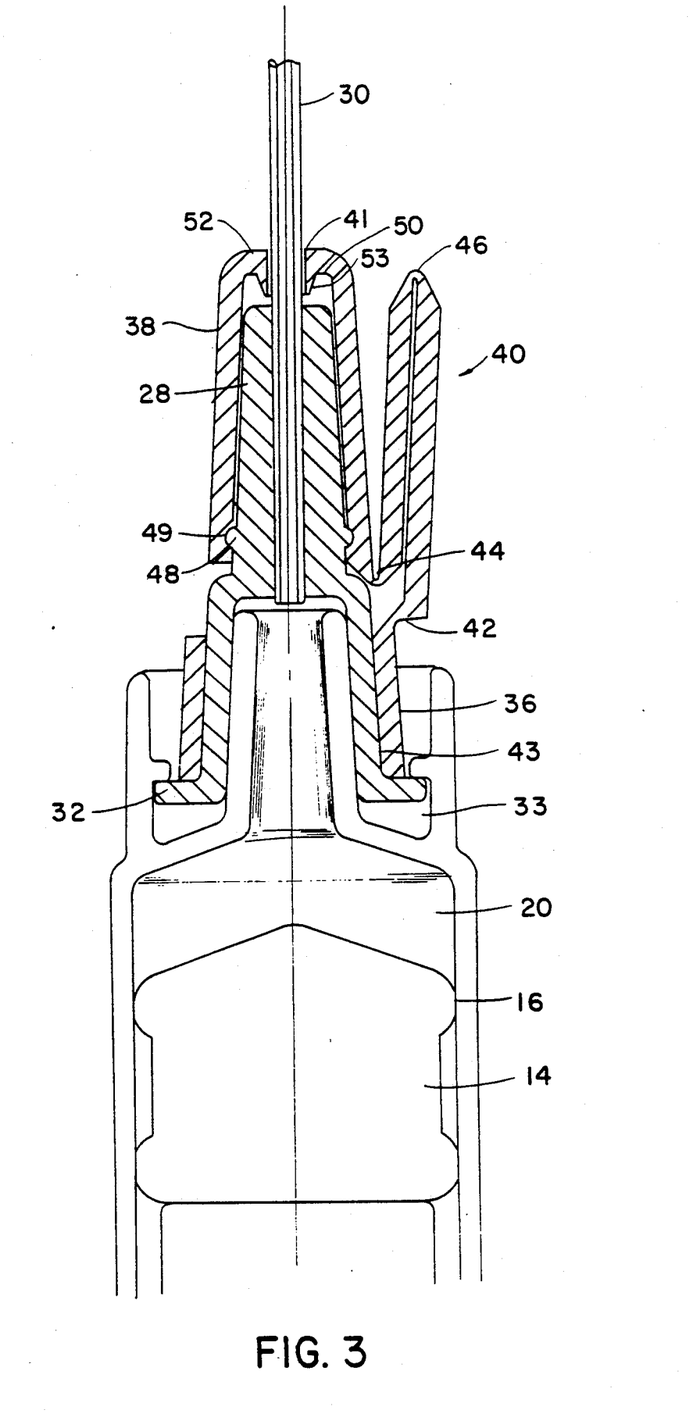
FIG. 3 is a cross-section view of another embodiment of the invention employing a single-winged cap with the wing folded upwards to facilitate packaging.

Referring to FIG. 3, the cover 34 may be provided with a single arm 40 which operates in the same manner as the double arm embodiment shown in FIGS. 1 and 2. As the cover 34 is raised above and over the needle 30, the cover will cock away from this side of arm 40 causing the needle to rest on the interior surface 50 of the same side as the arm 40. The tapered side 53 may be employed to prevent reemergence of the needle 30 as described previously.

Furthermore, it may be desirable to package the cover 34 with the arms 40 extending axially and substantially parallel -to the top portion 38 of the cover 34 as shown in the one arm embodiment of FIG. 3. By positioning the arms 40 in this manner, the radial dimension of the cover 34 is significantly reduced thereby minimizing the size of the packaging. As is apparent from a comparison of FIGS. 2 and 3, the arms 40 may be easily moved from the axially extending position shown in FIG. 3 to the radially extending position shown in FIG. 2 by exerting downward pressure on the arms 40 in the general of hinge 46.

Figure 4:
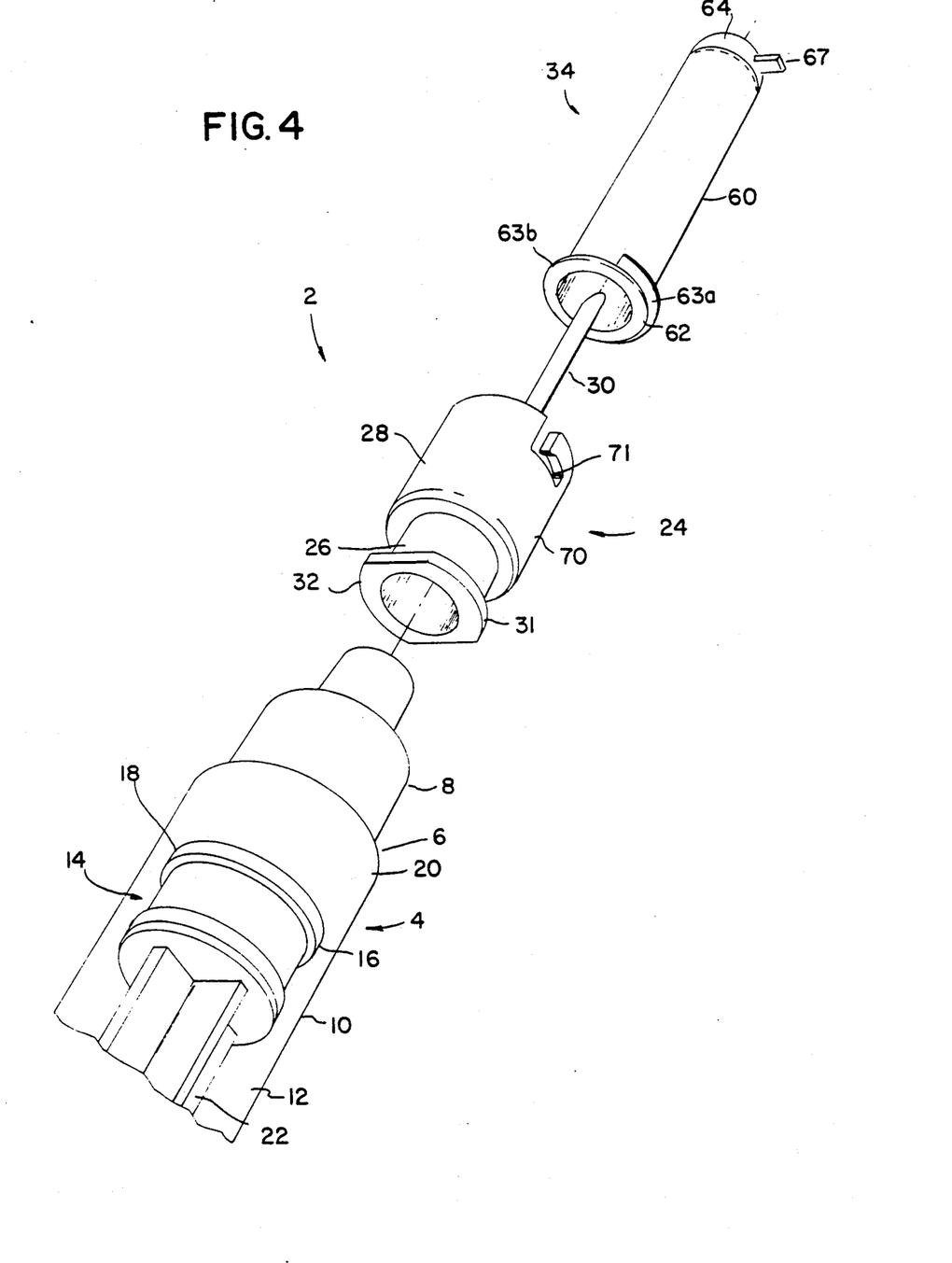
FIG. 4 is a partial exploded view of another embodiment of a syringe in accordance with the present invention employing a cap for covering the syringe.
Figure 5:
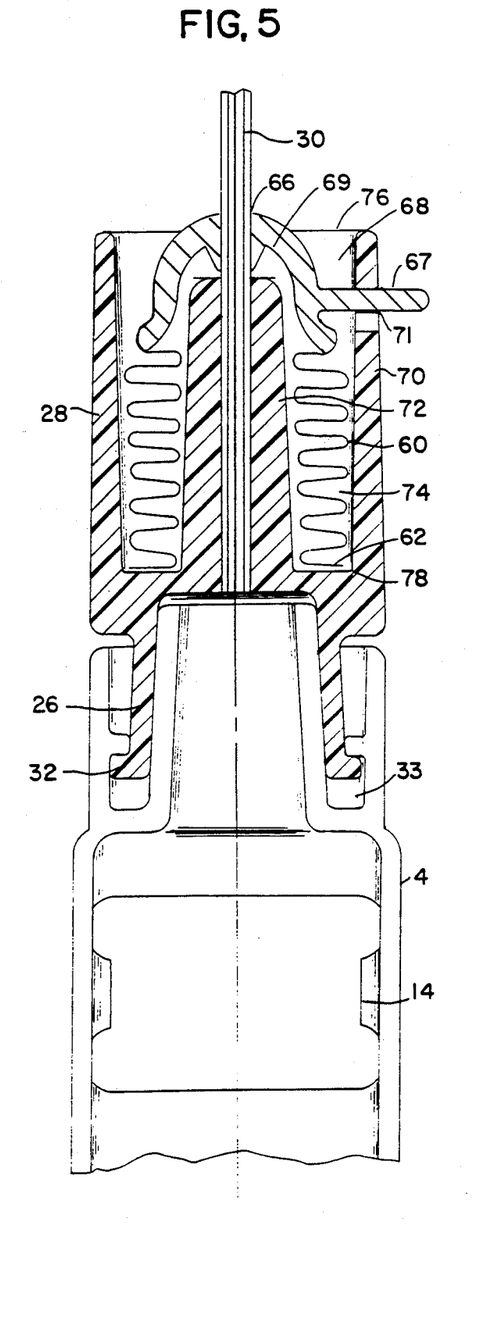
FIG. 5 is a partial cross-section view of the embodiment shown in FIG. 4.
Figure 6:
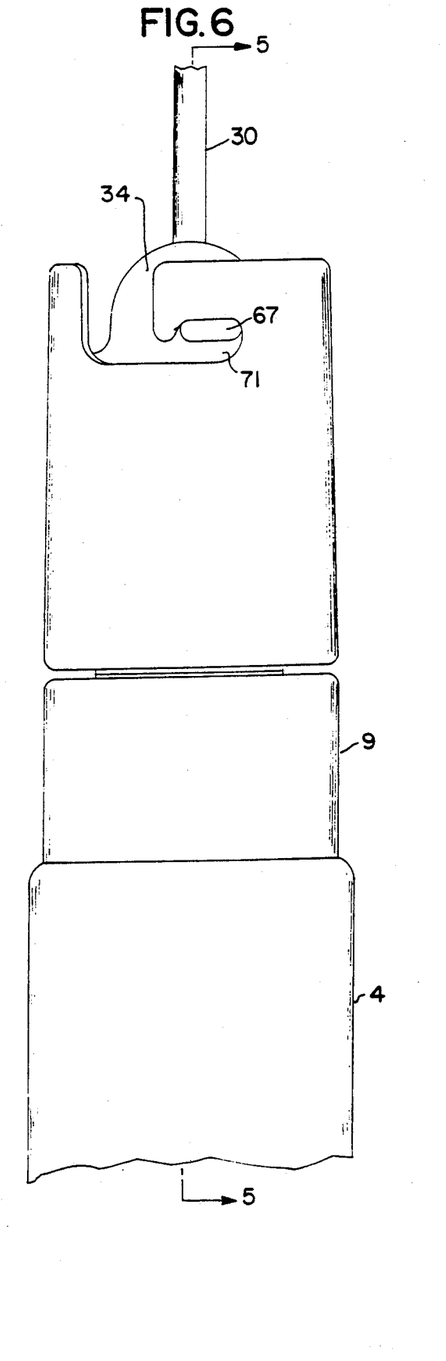
FIG. 6 is a side view of the embodiment shown in FIG. 4 showing the means for retaining the needle in the exposed position.

Referring to FIGS. 4 through 6, another embodiment is shown where the cover 34 comprises a cylindrical elastic body 60 having a flanged base 62 and a rigid top end 64 having an aperture 66 for receiving the needle 30. The top end 64 also has a radially extending projection 67.

The needle assembly 24 includes the base 26 and neck 28. The needle assembly 24 also includes a securing means 32 including an arcuate side surface 31 which serves as a thread that may be reversibly locked within a groove 33 as described in connection with FIGS. 1 through 3. The neck includes an outer wall 70, an inner needle mounting support 72 (See FIG. 5) which surrounds and supports the needle 30. The outer wall 70 has a slot 71 for receiving the projection 67.

Between the outer wall 70 and the needle support 72 is an annular cavity 74 having a top open end 76 and a closed bottom end 78. The cover 34 is adapted to be inserted and secured within the cavity 74. The flanged base 62 is secured, preferably with the use of an adhesive, to the closed bottom end 78 of the cavity 74.

Due to the elasticity of the body 60, the body 60 can be compressed into the retracted position as shown in FIGS. 5 and 6 thereby exposing the needle 30. The needle assembly 24 and the cover 34 may be shipped assembled, compressed, and covered with an elongated needle cap (not shown). In this position, the projection 67 is secured within the slot 71. After use of the needle 30, the contaminated needle 30 is covered by disengaging the projection 67 from the slot 71 which causes the elastic body 60 to move to the extended position above and over the contaminated needle 30.

Means are provided for preventing the contaminated needle 30 from reentering the aperture 66 after the cover 34 has been released to the extended position as shown in FIG. 4.

This can be accomplished, for example, by providing the flanged base 62 with an asymmetric width. More specifically, one portion 63a of the flanged base 62 has a width greater than the remaining portion 63b of the flanged base 62 as shown best in FIG. 4. As a result, one side of the elastic body 60 (the right side as shown in FIG. 4) is more tightly compressed than the opposed side of the elastic body 60. When the projection 67 is released from the slot 71, the cover 34 will rise above the needle 30 and move radially to the left because of the difference in compression between the right side of the body 60 and the left side. This is due to the shorter distance between the top surface of the flange portion 63a and the top of the cover 34, than the corresponding distance between the flange portion 63b and the top of the cover 34. As a result, the cover 34 will cock over to the left of the needle 30 once the cover 34 rises above the needle 30. The aperture 66 may also be provided with a conical tapered side 69 which prevents the needle 30 from reentering the aperture 66 as described previously in connection with FIG. 2.

The embodiment of FIGS. 4 through 6 can be manufactured as individual components or as a self-contained unit as described previously. In each case, a protective elongated snap-on cap is provided to cover the needle 30 before it is used.

Referring to FIGS. 7 through 12, embodiments of an externally loaded forward mounting needle assembly 24 are shown in which the needle assembly 24 is retracted within the barrel section 4 of the fluid passing device 2. In the embodiment shown in FIGS. 7 and 8, the needle assembly 24 is provided with a flange 90 between the base 26 and the neck 28. The flange 90 is adapted to engage under slight pressure the interior surface 92 of the collar 8 to provide axial guide means for the needle assembly 24. The base 26 is also provided with a projection 93 which is prevented from upward movement by a radially inwardly extending flange 95 on the interior surface 92 of the collar 8.

Figure 7:
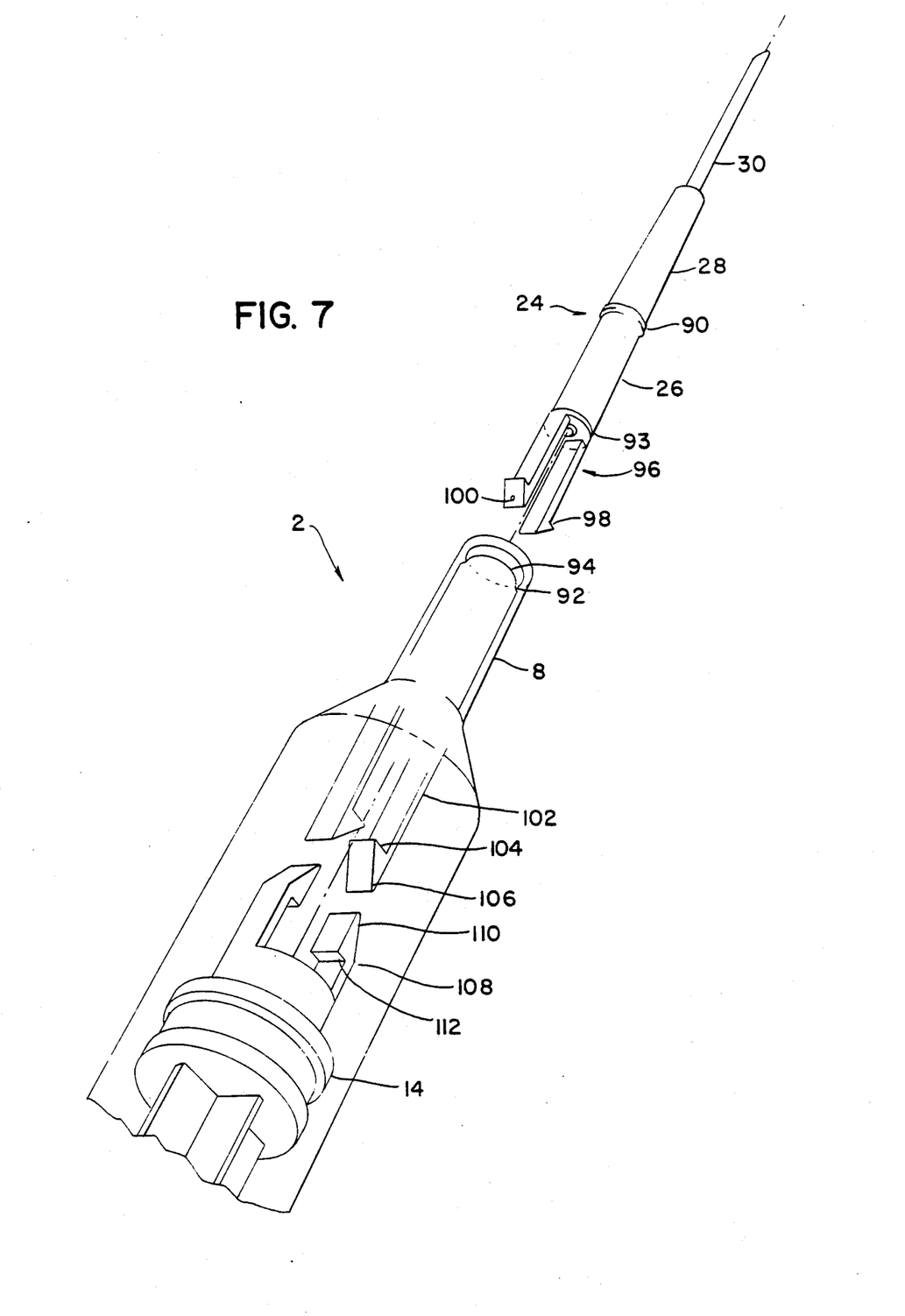
FIG. 7 is a partial exploded view of another embodiment of a syringe in which the needle assembly is retracted within the barrel.
Figure 8:
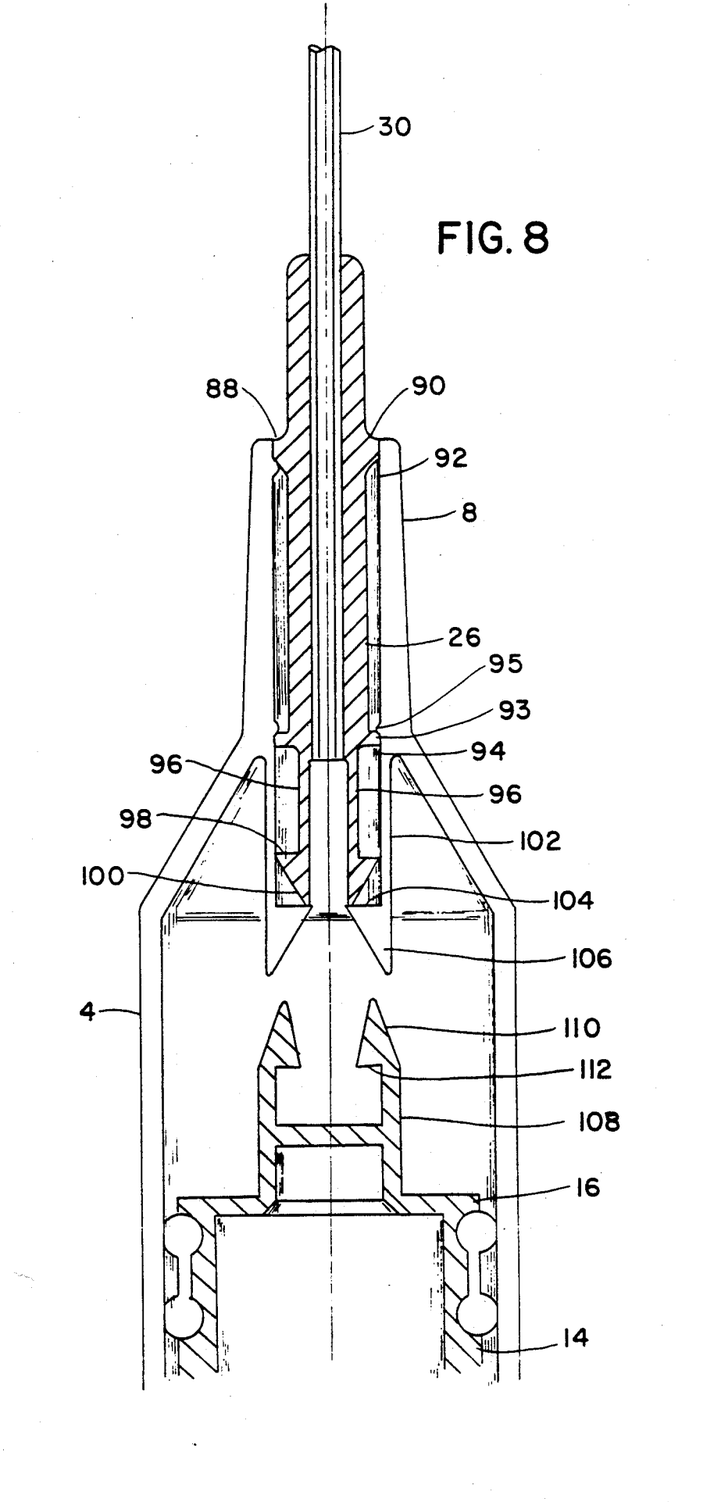
FIG. 8 is a partial cross-sectional view of the embodiment shown in FIG. 7.

The base 26 of the needle assembly 24 is also provided with a pair of spaced-apart downwardly extending detents 96 having radially outwardly extending ledges 98 and tapered ends 100. The detents 96 extend downwardly towards the barrel 4. Extending downwardly from the bottom of the collar 8 into the barrel section 4 are a pair of spaced-apart detents 102 having radially inwardly extending ledges 104 and tapered ends 106. The ledges 104 of the detents 102 provide a stop and support for the detents 96 when the needle assembly 24 is inserted into the collar 8 and when the needle 30 is injected into the patient so that the needle assembly 24 is prevented from downward movement into the barrel 4 when used to inject or withdraw a fluid from a patient.

The head section 16 of the plunger 14 is provided with a pair of spaced-apart upwardly extending detents 108 having tapered ends 110 and radially inwardly extending ledges 112.

In operation, at the end of the injection stroke the detents 108 are moved upward in the barrel section 4 until the ends 110 press against the ends 106 of the detents 102 forcing them radially outward and further apart. As a result, the ends 100 of the detents 96 are dislodged from their supported position on the ledges 104 of the detents 102. Continued upward movement of the plunger 14 causes the ledges 112 of the detents 108 to engage the ledges 98 of the detents 96 extending from the needle assembly 24. The plunger 14 is then pulled back and thereby retracts the needle assembly 24 into the barrel section 4.

Means may also be provided for misaligning the axis of the needle 30 after retraction to prevent the needle 30 from reentering the aperture 88 of the syringe. For example, one of the detents 108 or one of the detents 96 may be made slightly longer than the other detent 96 so that the needle 30 is caused to cock to one side of the barrel 4 upon retraction. Once the needle 30 is cocked to one side and fully withdrawn into the barrel 4, it is prevented from reentering the aperture 88 by the downwardly extending detent 102.

Figure 9:
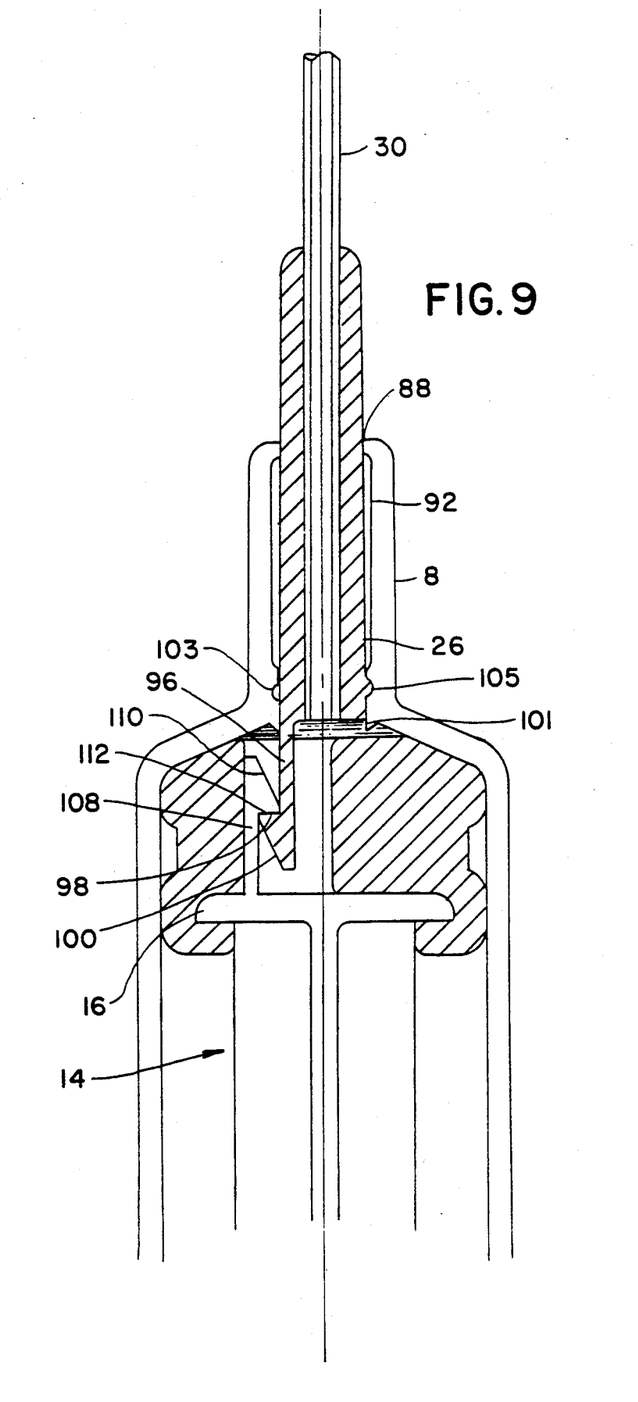
FIG. 9 is a partial cross-sectional view of another embodiment of a syringe in which the needle assembly is retracted within the barrel.

As shown in FIG. 9, the base 26 of the needle assembly 24 may-be provided with a single downwardly extending ledge 98 and a tapered end 100. The head section 16 of the plunger 14 is provided with a single upwardly extending detent 108 having a tapered end 110 and a radially inwardly extending ledge 112.

The collar 8 is provided with a downwardly extending annular lip 101 which serves to prevent the needle 30 from reentering the aperture 88 in the collar 8 after the needle 30 has been retracted.

As shown in FIG. 9, the entire needle assembly 24 is withdrawn into the barrel section 4. In order to secure the needle assembly 24 within the collar 8 prior to retraction so that injection or withdrawl of fluid can be made, the base 26 is provided with a radially extending flange 103 which is releasably secured in a recess 105 of the internal surface 92 of the collar 8.

In operation, at the end of the injection stroke the plunger 14 is moved upward so that the detent 108 is likewise moved upward in the barrel section 4 until the tapered end 110 presses against the end 100 of the downwardly extending detent 96. Continued upward movement of the plunger 14 causes the ledge 112 of the detent 108 to engage the ledge 98 of the detent 96 extending from the needle assembly 24.

The plunger 14 is then pulled back thereby dislodging the flange 103 from the recess 105 enabling the needle assembly 24 to be retracted within the barrel section 4. By positioning the detents 96 and 108 off the center axis of the barrel section 4 and needle assembly 24, the tip of the needle 30 will cock to (i.e. towards the left as shown into FIG. 9) as it passes in the barrel section 4 and will be prevented from reentering the collar 8 by the annular lip 101 as described previously.

Figure 10:
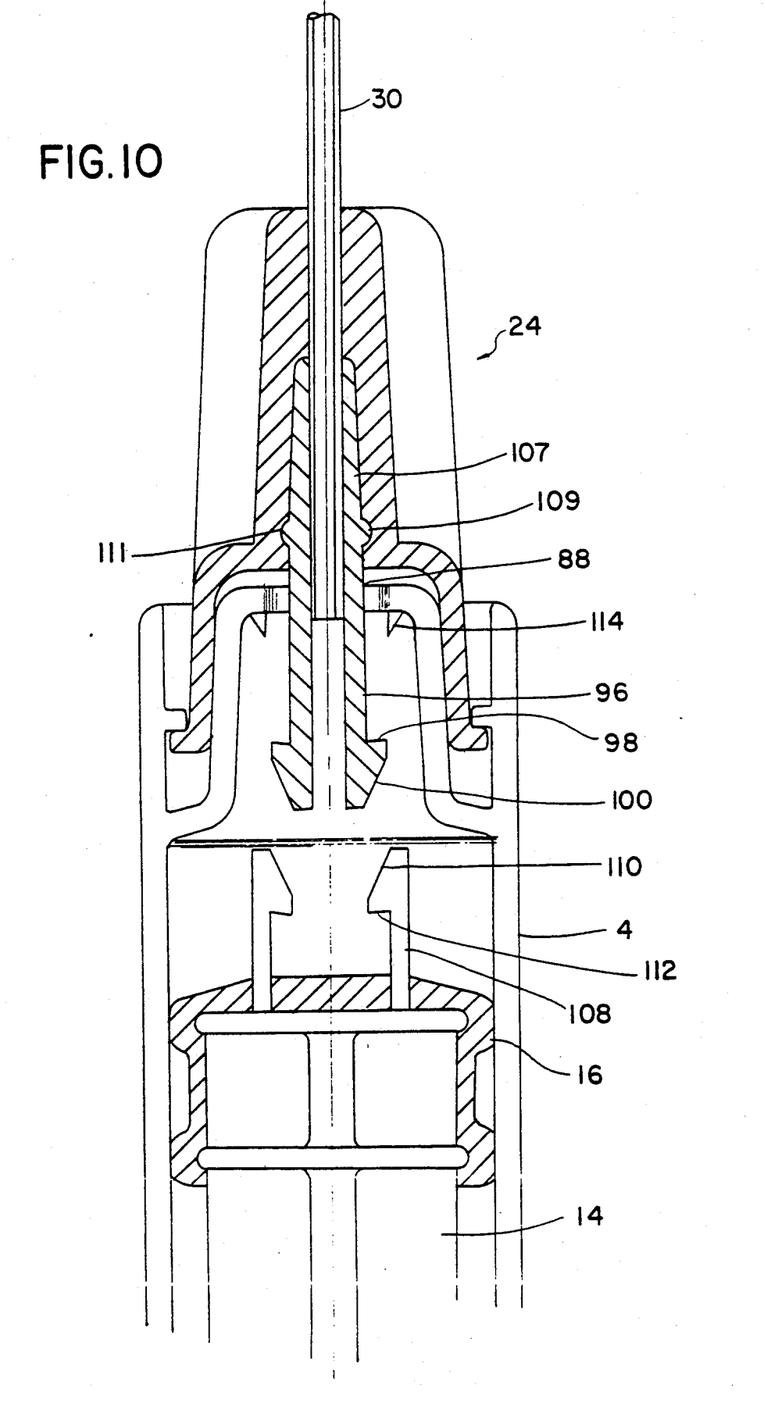
FIG. 10 is a cross-sectional view of still another embodiment of a syringe in which the needle assembly is retracted within the barrel.

Another embodiment of the invention employing a square cross-sectional barrel section 4 is shown in FIG. 10. The needle assembly 24 is secured to the barrel section 4 by a thread and groove. The needle assembly 24 includes a sheath 107 in which is secured the needle 30. The sheath 107 has thereon a flange 109 releasably secured in a recess 111. The head section 16 of the plunger 14 is provided with a pair of spaced-apart upwardly extending detents 108 having tapered ends 110 and radially inward extending ledges 112.

The sheath 107 of the needle assembly 24 is provided with a pair of spaced-apart downwardly extending detents 96 having radially outwardly extending ledges 98 and tapered ends 100.

When the upwardly extending detents 108 engage the downwardly extending detents 96, and the detents 96 are pulled downwardly, the flange 109 disengages from the recess 111 thereby allowing the sheath 107 and needle 30 to be retracted within the barrel section 4.

The aperture 88 in the barrel section 4 may be provided with a conical tapered side 114 to prevent reentry of the needle 30 after it has been retracted as previously described.

Figure 11:
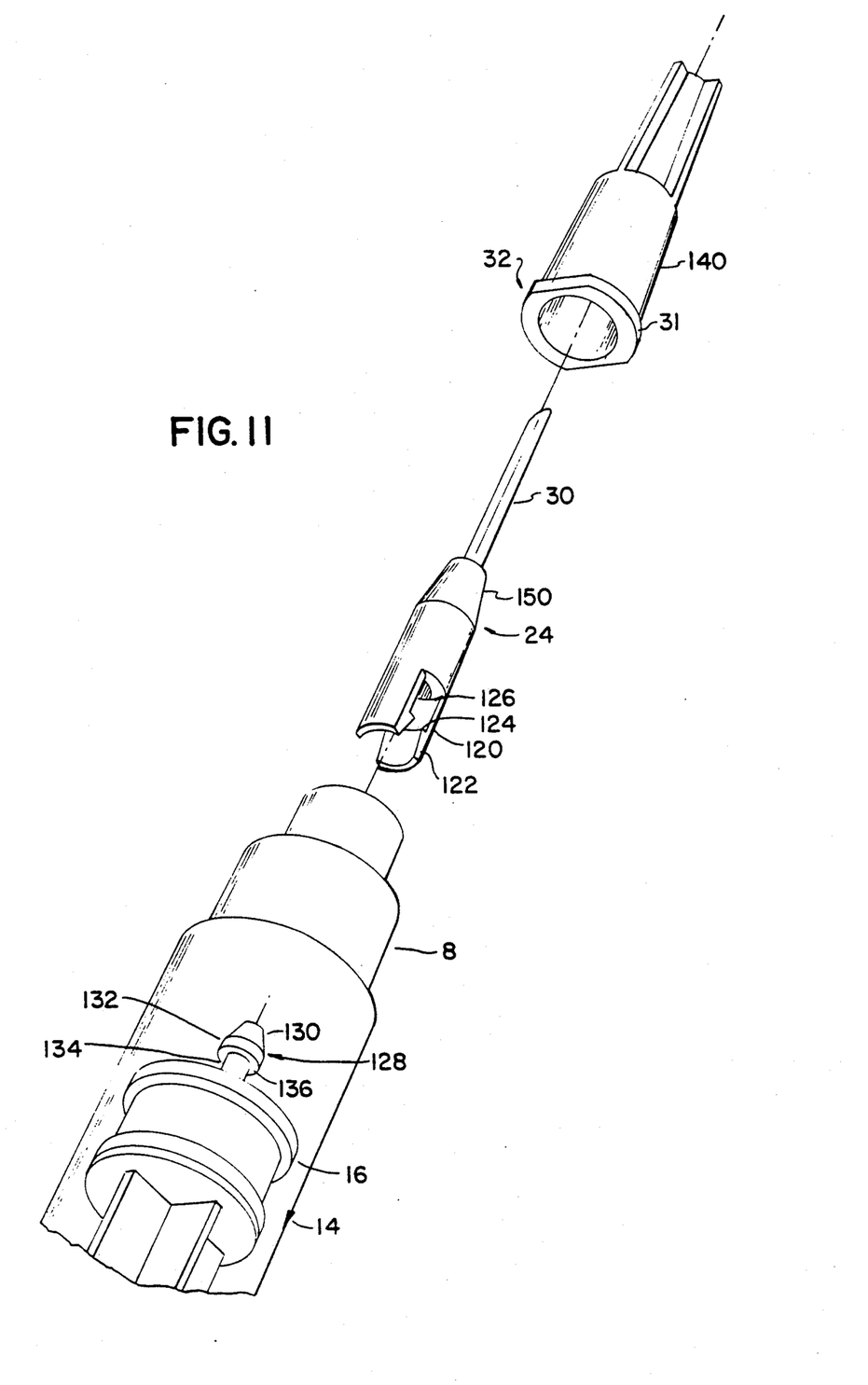
FIG. 11 is partial exploded view of a further embodiment of a retractable syringe in which the needle assembly is retracted within the barrel.
Figure 12:
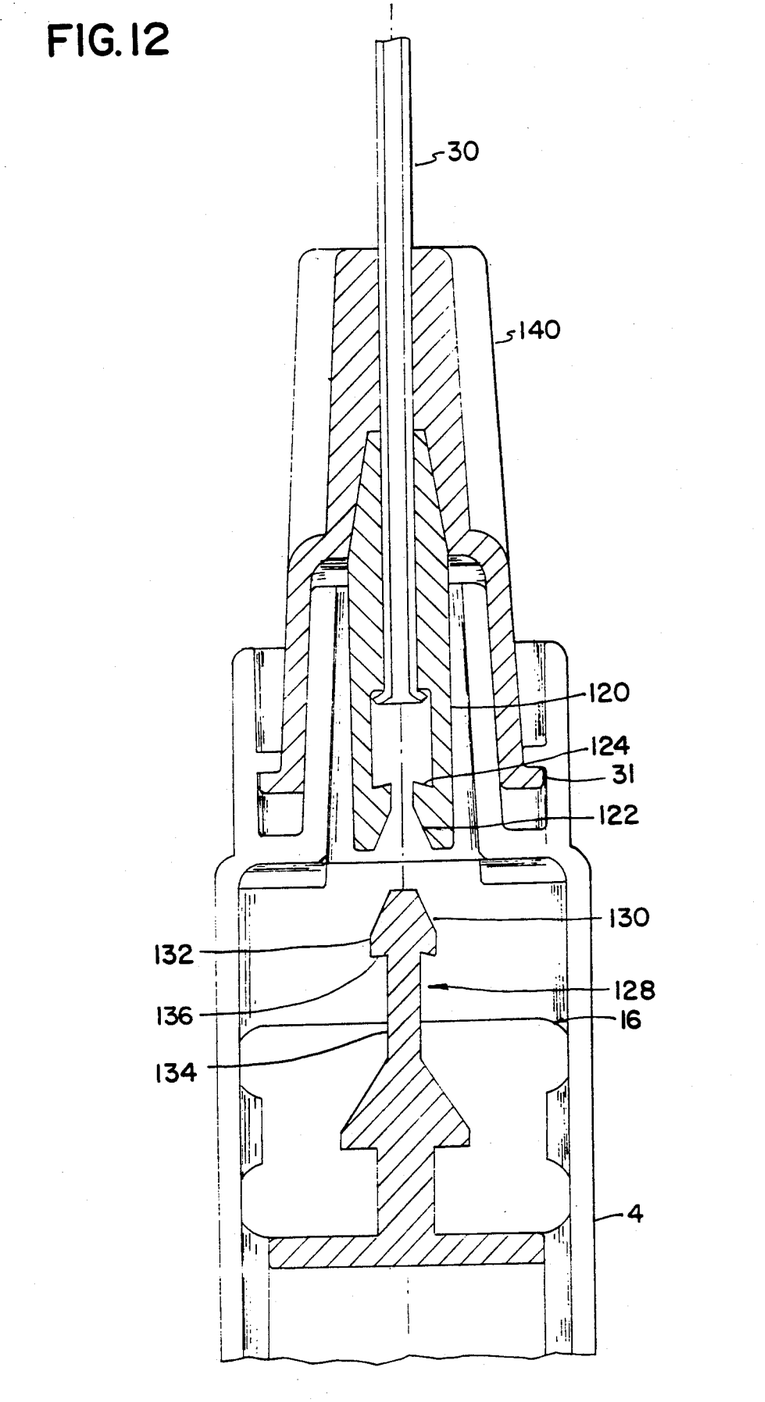
FIG. 12 is a cross-sectional view of the embodiment shown in FIG. 11.

Referring to FIGS. 11 and 12, another embodiment of the retractable needle assembly type is shown. The needle assembly 24 is provided with a pair of spaced apart downwardly extending detents 120, each having a tapered end 122 and a ledge 124 and an area 126 above the ledges 124 for receiving the head of a corresponding detent attached to the top surface of the head section 16 of the plunger 14.

More specifically, the head section 16 is provided with a single upwardly extending detent 128 having a conical head 130 and a cylindrical base 132. The detent 128 is connected to the head section 16 by a stem 134. The stem 134 has a cross-sectional dimension less than that of the base 132 so that the detent 128 has a radially extending surface 136 which is adapted to engage the ledges 124 of the detents 120

The needle assembly 24 is secured within an elongated needle assembly sleeve 140 having a securing means 32 including an arcuate surface 31 adapted to reversibly screw into the collar 8 as previously described. The needle assembly 24 is provided with a tapered head section 150 which is adapted to reversibly friction lock the needle assembly 24 within the sleeve 140, or otherwise releasably secure the needle assembly 24 within the sleeve 140.

As shown best in FIG. 12, as the plunger 14 is moved toward the peak of the injection stroke, the detent 128 extending upwardly from the head 16 of the plunger 14 engages the tapered sides 122 of the detents 120 and forces them apart. At about the peak of the injection stroke the surface 136 of the detent 128 rests upon the ledges 124 of the detents 120. As the motion of the plunger 14 is reversed (i.e., retracted within the barrel), the detent 128 pulls the detents 120 downwardly thereby releasing the needle assembly 24 from the sleeve 140 and retracting the needle assembly 24 within the barrel section 4.

The aperture of the barrel 4 may be provided with conical tapered sides (not shown) to prevent the needle from reentering the aperture as described previously in connection with the embodiments of FIGS. 9 and 10.

The relative position of the detents 120 may be angled with respect to the longitudinal axis of the needle assembly 24 to create an effective means of cocking the needle 30 as it is retracted into the barrel 4.

Figure 13:
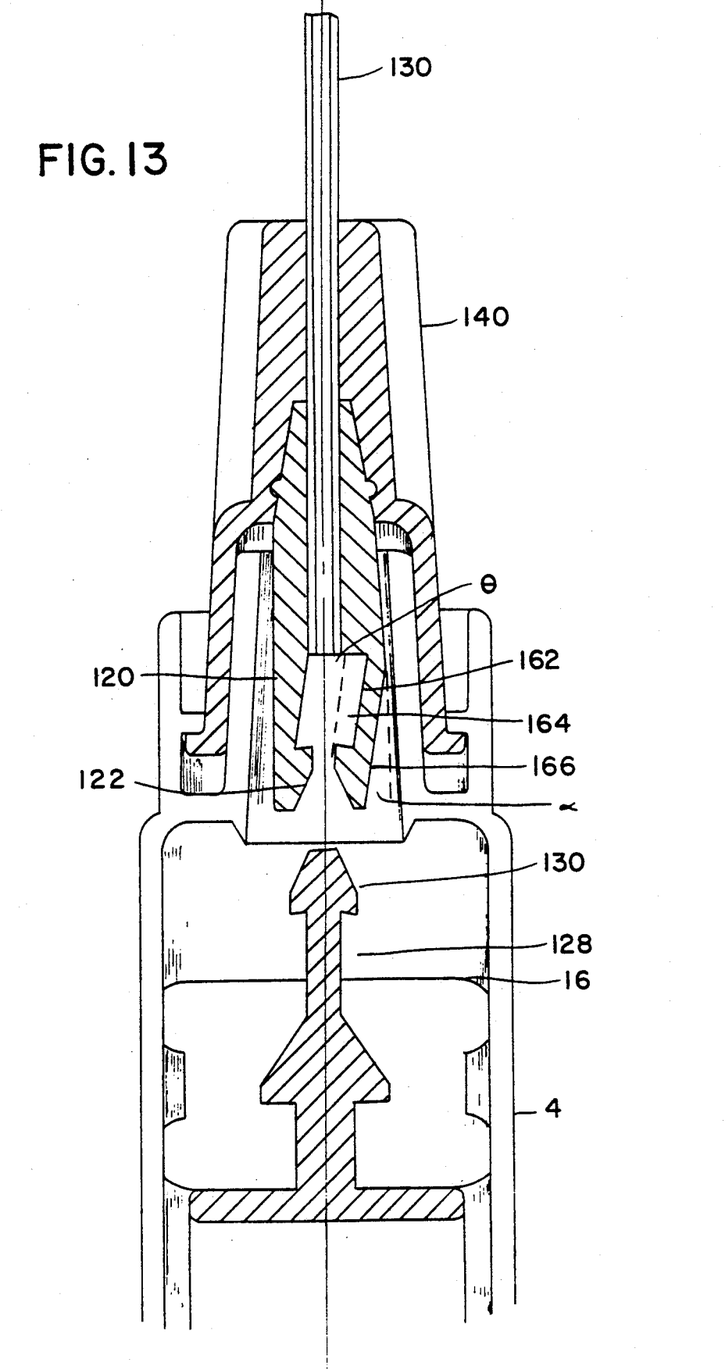
FIG. 13 is a cross-sectional view of an embodiment similar to the embodiment shown in FIGS. 11 and 12 with means for cocking the needle upon retraction into the barrel to prevent reentry.

Referring to FIG. 13, each of the detents 120 is provided with an inner side 162 which is angled with respect to longitudinal axis of the needle assembly 24 by an angle $\Theta$ which for practical purposes can be up to 45°, preferably in the range of about 10° to 25°. As a result, the space 164 between the respective detents 120 is essentially rectangular but may be constructed in any shape so long as the space 164 is sufficient to permit entry and engagement by the detent 128.

The outside surface 166 of one of the detents 120 (the right detent as shown in FIG. 13) tapers inwardly by an angle $\alpha$ which can be the same or different than the angle $\Theta$ described above. It is preferred for ease of construction that inner side 162 and outer side 166 are parallel (i.e. angle $\Theta$ = angle $\alpha$). The detents 120 are preferably made of a flexible plastic having a memory.

In operation, the detent 128 attached to the head 16 of the plunger 14 is moved into engagement with the detents 120. During this process the conical head 130 of the detent 128 engages and forces apart the tapered sides 122 of the detents 120 thereby forcing the outer side surface 166 of the right hand detent 120 to move from the angled position shown in FIG. 13 to a position where the outside surfaces 166 of each of the detents 120 are parallel to each other and to the longitudinal axis of the needle assembly 24 (i.e. angle $\alpha$ = 0°).

This procedure creates radial tension in the right hand detent 120 which seeks to return to its original angled position As the plunger 14 is retracted thereby pulling the needle assembly 24 downward into the barrel 4, the radial tension in the right hand detent 120 is transmitted to the needle assembly 24 causing the needle 30 to cock to the left. The cocked needle 30 is also prevented from reentering the aperture by conical tapered sides 101 as previously described in connection with FIG. 9 and 114 of FIG. 10 for example.

Figure 14:
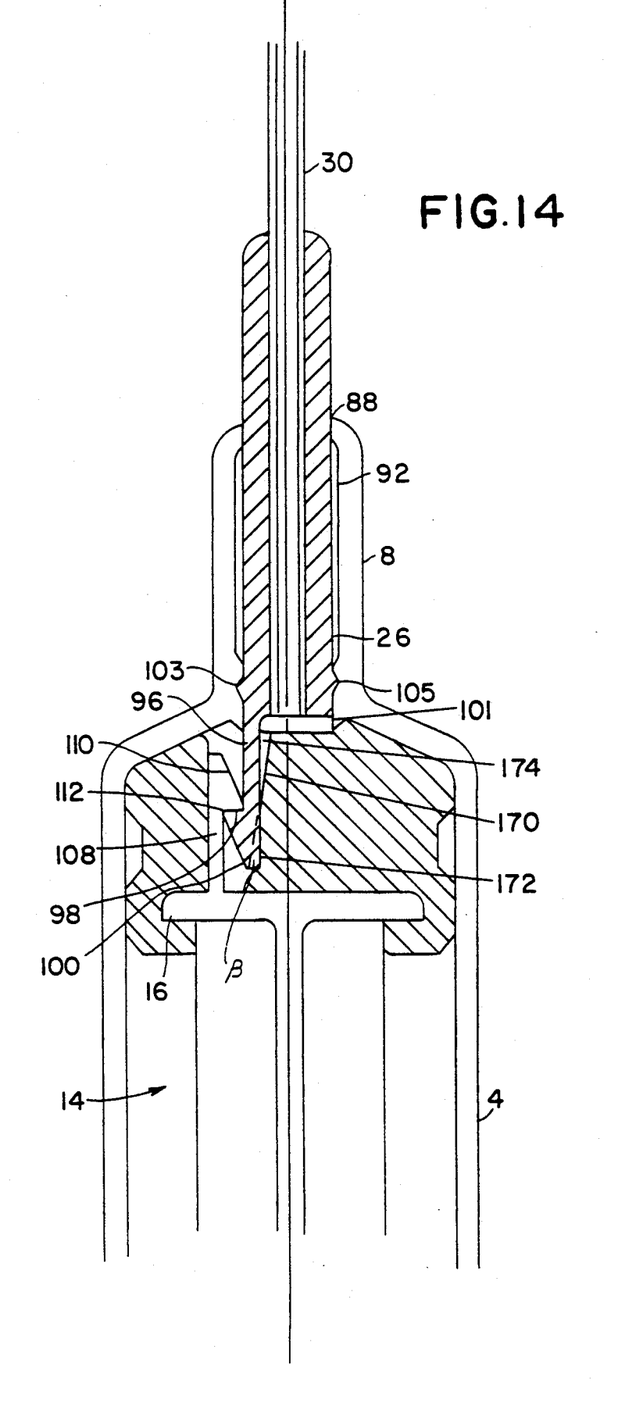
FIG. 14 is a cross-sectional view of another embodiment of the invention similar to FIG. 9 with an inner wall of the plunger adapted to push against the detent extending from the needle assembly whereby the needle assembly is cocked in the barrel as it is retracted.

Referring to FIG. 14 there is shown a modification of the embodiment described in connection with FIG. 9 in which the plunger itself cooperates to provide radial tension against the single downwardly extending detent which serves to facilitate cocking of the needle as it is retracted into the barrel.

More specifically, the plunger 14 is provided with an inner wall 170 which is tapered by an angle $\beta$ with respect to the longitudinal axis of the needle 30 and thereby creates radial tension against the side wall 172 of the downwardly extending detent 96 in a direction substantially perpendicular to the axis of the needle 30. In addition, a gap 174 is created between the respective upper portions of the detent 96 and the wall 170.

The angle of taper may be the same as that described previous for the angles $\Theta$ and $\alpha$ (i.e. up to 45°, preferably from about 10° to 25°). The detent 96 and the plunger wall 170 may preferably be made of a flexible plastic having a memory to facilitate the radial tension and eventual cocking of the needle 30 in the barrel 4.

The operation of the embodiment shown in FIG. 14 is similar to that described with respect to FIG. 9. Radial tension exists at the junction of the detent wall 172 and the plunger wall 170. As the needle 30 is drawn into the barrel 4 the detent 96 seeks to relieve the radial tension by moving to the right and thereby occupy the space of the gap 174 and is thereby cocked toward the right as the needle is fully retracted. The needle 30 is prevented from reentering the aperture 88 by the conical tapered sides 101 described previously.

The features shown in the embodiments described herein may be modified by those skilled in the art within the spirit and scope of the invention. For example, the needle assembly may be provided with more than two detents so long as the detents extending upwardly from the plunger are able to engage and draw the needle assembly downward within the barrel.

As previously indicated in connection with FIGS. 7, 8 and 10, the barrel 4 may have a rectilinear cross section so that the detents 108 extending upwardly from the plunger 14 are always precisely aligned with the downwardly extending detents 96. In this way, the user does not have to visually observe the movement of the plunger 14.

The present invention provides a novel and commercially viable means for covering a contaminated needle or other fluid passing device in which exposure to the contaminated needle is virtually eliminated and reentry of the needle in the aperture prevented. Additionally, the present invention retains the commercially required top loading exteriorly mounted needle assembly which allows for easy loading and interchangeability of needles.

What we claim is:

1. Apparatus for passing a fluid into or out of a warm-blooded animal or tissue thereof comprising:
   (a) a body adapted to contain said fluid;
   (b) fluid passing means comprising a base having a pair of opposed ends, needle means extending from one end of the base, means for releasably securing the other end of the base to the body, an exterior wall and an annular cavity formed between the base and the wall;
   (c) means for urging said fluid out of or into said body through the fluid passing means;
   (d) cover means comprising a cap having a body having a top end including an opening for receiving the needle means, a bottom end adapted to be secured within the annular cavity, and means for moving the body of the cap from a compressed position wherein the needle means extends through the opening in the top end of the cap and is in the operable position for passing fluid into or out of said warm-blooded animal, to an extended position wherein the cap moves upwardly and above the needle means thereby encasing the needle means within the cap; and
   (e) cap retaining means comprising a radially extending projection at the top end of the cap and a projection receiving slot in the wall of the fluid passing means, said projection being releasably retained in the slot when the cap is in the compressed position and movable out of the slot when the cap is moved to the extended position encasing the needle means.

2. The apparatus of claim 1 wherein the bottom end of the cap is secured within the annular cavity with an adhesive.

3. The apparatus of claim 1 wherein the cap body is made of a compressible material, said cap being movable from the compressed position within the annular cavity exposing the needle means to the extended position wherein a portion of the cap moves out of the cavity upwardly and above the needle means thereby encasing the needle means within the cap.

4. Apparatus for passing a fluid into or out of a warm-blooded animal or tissue thereof comprising:
   (a) a body adapted to contain said fluid;
   (b) fluid passing means comprising a base having a pair of opposed ends, needle means extending from one end of the base, means for releasably securing the other end of the base to the body, an exterior wall and an annular cavity formed between the base and the wall;
   (c) means for urging said fluid out of or into said body through the fluid passing means;
   (d) cover means comprising a cap having a body having a top end including an opening for receiving the needle means, a bottom end adapted to be secured within the annular cavity, and means for moving the body of the cap from a compressed position wherein the needle means extends through the opening in the top end of the cap and is in the operable position for passing fluid into or out of said warm-blooded animal, to an extended position wherein the cap moves upwardly and above the needle means thereby encasing the needle means within the cap; and
   (e) Offsetting means for offsetting the axis of the cap from the axis of the needle means when the cap is moved to the extended position encasing the needle means, whereby the needle means is prevented from reentering the opening in the top end of the cap, said offsetting means comprising said bottom end of the cap having a radially extending flange, a portion of the flange having a greater thickness than the remaining portion of the flange.

5. The apparatus of claim 4 wherein the bottom end of the cap is secured within the annular cavity with an adhesive.

6. The apparatus of claim 4 wherein the cap body is made of a compressible material, said cap being movable from the compressed position within the annular cavity exposing the needle means to the extended position wherein a portion of the cap moves out of the annular cavity upwardly and above the needle means thereby encasing the needle means within the cap.

7. The apparatus of claim 4 further comprising means in the exterior wall for releasably retaining the cap in the compressed position.

8. The apparatus of claim 7 wherein the cap retaining means comprises a radially extending projection at the top end of the cap and a projection receiving slot in the wall of the fluid passing means, said projection being releasably retained in the slot when the cap is in the compressed position and movable out of the slot when the cap is moved to the extended position encasing the needle means.

* * * * *